United States Patent [19]

Sarges et al.

[11] 4,181,728

[45] Jan. 1, 1980

[54] SPIRO-POLYCYCLICIMIDAZOLIDINEDIONE DERIVATIVES

[75] Inventors: Reinhard Sarges, Mystic, Conn.; John L. Belletire, Madison, Wis.

[73] Assignee: Pfizer Inc., New York, N.Y.

[21] Appl. No.: 961,335

[22] Filed: Nov. 16, 1978

[51] Int. Cl.$^2$ .................. C07D 491/10; C07D 495/10; C07D 235/02

[52] U.S. Cl. ................................ 424/273 R; 548/309; 548/308

[58] Field of Search ............................ 548/309, 308; 424/273 R

[56] References Cited

U.S. PATENT DOCUMENTS

| | | | |
|---|---|---|---|
| 2,683,718 | 1/1952 | Dornfield | 548/309 |
| 3,532,744 | 10/1970 | Fletcher et al. | 548/308 |
| 3,821,383 | 6/1974 | Sestanj et al. | 424/258 |
| 4,117,230 | 9/1978 | Sarges | 548/308 |
| 4,127,665 | 11/1978 | Sarges et al. | 548/309 |
| 4,130,714 | 12/1978 | Sarges | 548/309 |

FOREIGN PATENT DOCUMENTS

| | | | |
|---|---|---|---|
| 1032257 | 6/1955 | Fed. Rep. of Germany | 548/308 |
| 796069 | 6/1958 | United Kingdom | 548/308 |
| 818724 | 8/1959 | United Kingdom | 548/308 |

Primary Examiner—Natalie Trousof
Assistant Examiner—Jane T. Fan
Attorney, Agent, or Firm—F. X. Murphy; C. J. Knuth; A. J. Nelson

[57] ABSTRACT

Novel spiro-polycyclicimidazolidinedione derivatives useful as aldose reductase inhibitors and as therapeutic agents for the treatment of chronic diabetic complications are disclosed. The derivatives include 2',3'-dihydro-spiro[imidazolidine-4,4'-[4'H]-naphtho[1,2-b]pyran]-2,5-dione, 2',3'-dihydro-spiro-[imidazolidine-4,4'-[4'H]-naphtho[1,2-b]thiopyran]-2,5-dione, 1',2',3',4'-tetrahydro-spiro[imidazolidine-4,1'-benz[a]anthracene]2,5-dione, 2',3'-dihydro-spiro[imidazolidine-4,1'phenalene]-2,5-dione, 1',2',3',4'-tetrahydro-spiro[imidazolidine-4,1'-phenanthrene]-2,5-dione, the 2,1 isomers of the 2',3'-dihydro-4'H-pyran and 2',3'-dihydro-4'H-thiopyran derivatives, the 2',3'-dihydro-4'H-anthracenopyran and 2',3'-dihydro-4'H-anthracenothiopyran derivatives, the spiro-4,4' isomer of the tetrahydrophenanthrene derivative, the [b] isomer of the benzanthracene derivative and the mono or disubstituted 2',3'-dihydro-4'H-naphthopyran, 2',3'-dihydro-4'H-naphthothiopyran and tetrahydrophenanthrene derivatives.

11 Claims, No Drawings

SPIRO-POLYCYCLICIMIDAZOLIDINEDIONE DERIVATIVES

BACKGROUND OF THE INVENTION

This invention relates to novel spiro-polycyclicimidazolidinedione derivatives and their pharmaceutical formulations which are useful in the treatment of certain chronic complications arising from diabetes mellitus, such as diabetic cataracts and neuropathy.

Although many oral antidiabetic agents, such as the sulfonyl ureas, effectively lower blood sugar levels, the prevention or alleviation or the chronic complications of diabetes, such as diabetic cataracts, neuropathy, retinopathy and nephropathy has proved harder to achieve. According to the U.S. Pat. No. 3,821,383, aldose reductase inhibitors such as 1,3-dioxo-1H-benz[d,e]-isoquinoline-2(3H)-acetic acid and its derivatives are useful in this regard. Spiro-thienohydantoin derivatives are also aldose reductase inhibitors according to U.S. application Ser. No. 870,542. Such compounds inhibit the enzymatic reduction of aldoses, such as glucose and galactose, to the corresponding polyols, such as sorbitol and galactitol, thus preventing or reducing the harmful and unwanted accumulations of polyols in the lens and retina of the diabetically cataractous eye, in the diabetically neuropathic peripheral nerve and in the diabetically nephropathic kidney.

SUMMARY OF THE INVENTION

The compounds of the present invention are novel spiro-polycyclicimidazolidinedione derivatives of the formula

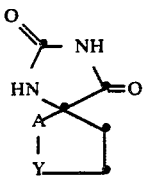

and the pharmaceutically acceptable metal salts thereof wherein
A is naphth-$\alpha,\beta$-o of the formula

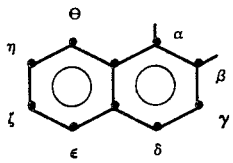

anthracen-$\alpha,\beta$-o of the formula

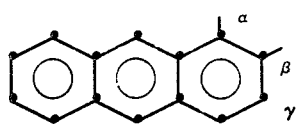

or substituted naphth-$\alpha,\beta$-o having 1 or 2 identical substituents selected from methyl, chloro or bromo; and
Y is $CH_2$, S, SO, $SO_2$ or O;
or A and Y taken together are naphth-$\alpha,\beta$-o of the formula

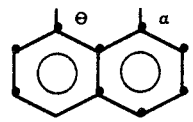

When A is naphth-$\alpha,\beta$-o, anthracen-$\alpha,\beta$-o or substituted naphth-$\alpha,\beta$-o, Y may be bonded to either the $\alpha$ or $\beta$ position of A. This type of attachment places the rings of A in either a syn or anti configuration with respect to the hydantoin or imidazolidinedione ring. For example bonding S to the $\alpha$ position of the naphth-$\alpha,\beta$-o produces anti configuration spiro-polycyclimidazolidinedione derivative B which is named 2′,3′-dihydro-spiro[imidazolidine-4,4′-[4′H]-naphtho[1,2-b]thiopyran]-2,5-dione.

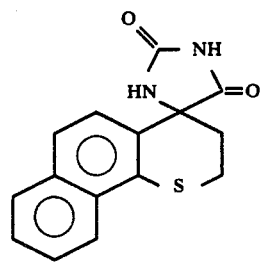

Bonding S to the $\beta$ position produces syn configuration derivative C which is named 2′,3′-dihydro-spiro[imidazoline-4,4′-[4′H-naphtho[2,1-b]thiopyran]-2,5-dione.

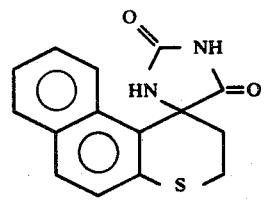

When A and Y together are naphth-$\alpha,\theta$-o, the resulting spiro-polycyclicimidazolinedione derivative D is named 2′,3′-dihydro-spiro[imidazoline-4,1′-phenalene]-2,5-dione and has the structure:

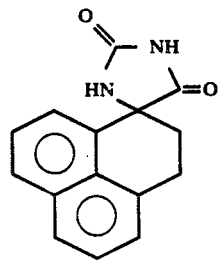

A preferred polycyclicimidazolidinedione derivative of the present invention is that of formula I wherein A is naphth-$\alpha,\beta$-o and Y is $CH_2$, S or O. Another preferred derivative of the present invention is that of formula I wherein A is $\epsilon$-methoxynaphth-$\alpha,\beta$-o or $\delta$-chloronaphth-$\alpha,\beta$-o and Y is $CH_2$, S or O.

Especially preferred embodiments include 2′,3′-dihydro-spiro[imidazolidine-4,4′-[4′H]-naphtho[2,1-b]thiopyran]-2,5-dione wherein A is naphth-α,β-o, Y is S and S joins the naphth-α,β-o at the β position;

2',3'-dihydro-7'-methoxy-spiro[imidazolidine-4,4'-[4'H]-naphtho[1,2-b]pyran]-2,5-dione wherein A is ε-methoxynaphth-α,β-o, Y is O and O joins the ε-methoxynaphth-α,β-o at the α position;

2',3'-dihydro-spiro[imidazolidine-4,4'-[4'H]-naphtho[1,2-b]thiopyran]-2,5-dione wherein A is naphth-α,β-o, Y is S and S joins the naphth-α,β-o at the α position;

2',3'-dihydro-spiro[imidazolidine-4,1'-phenalene]-2,5-dione wherein A and Y taken together are naphth-α,θ-o, 2',3'-dihydro-spiro[imidazolidine-4,4'-[4'H]-naphtho[1,2-b]pyran]-2,5-dione wherein A is naphth-α,β-o, Y is O and O joins the naphth-α,β-o at the α position;

6-chloro-4'H-2',3'-dihydro-spiro[imidazolidine-4,4'-naphtho[1,2-b]pyran]-2,5-dione wherein A is δ-chloronaphth-α,β-o, Y is O and O joins the δ-chloronaphth-α,β-o at the α position; and 1',2',3',4'-tetrahydro-spiro[imidazolidine-4,1'-phenanthrene]-2,5-dione wherein A is naphth-α,β-o, Y is CH₂ and CH₂ joins the naphth-α,β-o at the α position.

The present invention includes a method of treating a diabetic host to inhibit harmful, in vivo enzymatic reduction of aldoses or to prevent or alleviate diabetes-associated complications, such as cataracts, neuropathy, nephropathy or retinopathy. This treatment is accomplished by administering to the host an effective amount of a derivative of formula I. Also included is the formulation of a pharmaceutically-acceptable carrier material and a spiro-polycyclicimidazolidinedione derivative of formula I in an amount effective to inhibit harmful, in vivo enzymatic reduction of aldoses or to prevent or alleviate diabetes-associated complications, such as cataracts, neuropathy, nephropathy or retinopathy.

DETAILED DESCRIPTION OF THE INVENTION

The novel polycyclimidazolidinedione derivatives of the present invention are readily prepared from appropriate ketones of formula II

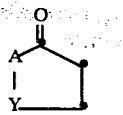

II wherein A and Y are as previously defined. For example imidazolidinedione derivative B above is prepared from its starting material ketone of the formula

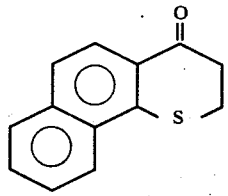

Likewise, imidazolidinedione derivative D above is prepared from its starting material ketone of the formula

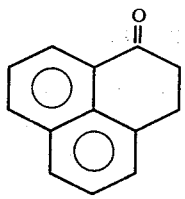

To synthesize an imidazolidinedione derivative the ketone (formula II) is condensed with an alkali metal cyanide, such as sodium cyanide or potassium cyanide, and ammonium carbonate. The reaction is normally conducted in the presence of a reaction-inert polar organic solvent in which both the reactants and reagents are mutually miscible. Preferred organic solvents include, but are not limited to, cyclic ethers such as dioxane and tetrahydrofuran, lower alkylene glycols such as ethylene glycol and trimethylene glycol, water-miscible lower alkanols such as methanol, ethanol and isopropanol, and N,N-di(lower alkyl)lower alkanoamides such as N,N-dimethyl formamide, N,N-diethyl formamide and N,N-dimethyl acetamide. In general, the reaction is conducted at a temperature from about 50° C. to about 150° C., preferably about 90° C. to 130° C., for a period of about 2 hours to about 4 days, depending on the temperature employed. Although the amount of reactants and reagents employed in the reaction must at least be present in a stoichiometric amount, it is preferable to employ a moderate molar excess of the alkali metal cyanide and ammonium carbonate reagents with respect to the ketone starting material in order to achieve maximum yield. Upon completion of the reaction, the desired product is readily isolated using conventional techniques. For example the reaction mixture may be diluted with water and the resultant aqueous solution cooled to room temperature, followed by acidification to afford the desired spiro-polycyclicimidazolidinedione derivative.

The starting material ketones of formula II are readily available or can be prepared by methods known to those skilled in the art. A typical preparative method consists of a Friedel-Crafts ring closure of 4-(1 or 2-naphthyl or anthracenyl) butyric acid, 3-(1 or 2-naphthoxy or naphthylthio) propionic acid or the mono or disubstituted forms of the naphthyl, naphthoxy or naphthylthio compounds wherein the substituents are as defined above to form the desired cyclohexanone, 4H-2,3-dihydropyran-4-one or 4H-2,3-dihydrothiopyran-4-one ring. The acids in turn are formed from condensation of the appropriate naphthalene or anthracene compound with butyrolactone or from condensation of the appropriate naphthol or thionaphthol with acrylonitrile under basic conditions followed by hydrolysis of the resulting 3-(1 or 2-naphthoxy or naphthylthio) propionitrile. For example, condensation of 5-chloronaphth-1-thiol with acrylonitrile in the presence of a base such as benzyltrimethylammonium hydroxide followed by hydrolysis with an acid or base produces 3-(5-chloronaphthyl-1-thio) propionic acid. The Friedel-Crafts reaction is then performed upon the acid using a reagent such as polyphosphoric acid which fuses the propionic acid fragment to the naphthyl ring to produce 7-chloro-4H-2',3-dihydronaphtho[2,1-b]thiopyran-4-one.

Pharmaceutically acceptable metallic salts can be readily prepared from compounds of formula I by conventional methods. Treatment of a spiro-polycyclicimidazolidinedione derivative with an aqueous solution of the desired pharmaceutically acceptable metallic hydroxide or other metallic base and evaporation of the resulting solution to dryness, preferably under reduced pressure, will afford the salt. Alternatively, a lower alkanol solution of a spiro-polycyclicimidazolidinedione derivative may be mixed with an alkoxide of the desired metal followed by evaporation of the alcohol solvent. The pharmaceutically acceptable metallic hydroxides, bases and alkoxides include those with cations that form metallic salts with the acidic compounds of formula I and that are non-toxic at the dosages administered to a subject in need of treatment. Suitable cations include, but are not limited to, potassium, sodium, ammonium, calcium and magnesium.

The novel spiro-imidazolidinedione derivatives of this invention are useful as aldose reductase inhibitors, and as such are of therapeutic value in the prophylactic and remedial treatment of chronic complications of diabetes, such as cataracts, retinopathy, nephropathy and neuropathy. The compounds may be administered to a subject in need of treatment by a variety of conventional routes of administration, such as oral, intraveneous, intramuscular, subcutaneous, topical, opthalmic and intraperitoneal. In general, these compounds will be administered at dosages between 1 and 250 mg per kg body weight of the subject to be treated per day. However, the particular dose, formulation and route of administration depend upon each patient's unique condition and the wisdom of his attending physician.

The compounds may be administered alone or in combination as a pharmaceutical formulation using pharmaceutically acceptable carrier material such as inert solid diluents, aqueous solutions or various non-toxic, organic solvents in dosage forms such as gelatin capsules, tablets, powders, lozenges, syrups, injectable solutions and the like. Such formulation material includes water, ethanol, gelatins, lactose, starches, vegetable oils, petroleum jelly, gums, glycols, talc, benzyl alcohols and other known carriers for medicaments. If desired, these pharmaceutical formulations may contain auxillary material such as preserving agents, wetting agents, stabilizing agents, lubricating agents, absorption agents, buffering agents and isotonic agents.

The ability of the spiro-polycyclicimidazolidinediones of the present invention to control chronic diabetic complications may be determined by a number of standard biological or pharmacological tests. These include (1) measuring the ability to inhibit the enzyme activity of isolated aldose reductase; (2) measuring the ability to reduce or inhibit sorbitol accumulation in the sciatic nerve of acutely streptozotocinized (i.e., diabetic) rats; (3) measuring the ability to reverse already-elevated sorbitol levels in the sciatic nerve and lens of chronic streptozocin-induced diabetic rats; (4) measuring the ability to prevent or inhibit galactitol formation in the lens of acutely galactosemic rats; and (5) measuring the ability to delay cataract formation and reduce the severity of lens opacities in chronic galactosemic rats.

The present invention is exemplified by the preparation of several spiro-polycyclicimidazolidinedione derivatives and by their biological activities in tests 1 and 2 above. It will be understood, however, that the invention is not limited to the specific details given.

GENERAL PROCEDURE FOR PREPARATION

The Examples of spiro-polycyclicimidazolidinedione derivatives given below in Table 1 were synthesized from the appropriate ketone of formula II above using the following general preparation procedure.

About 1 g of the starting material ketone, $\frac{1}{2}$ to 3 g of potassium cyanide, 2 to 10 g of ammonium carbonate, 10 to 25 ml ethanol and 0 to 25 ml water were heated at 100° to 130° in a steel bomb for 15 to 72 hours. The reaction mixture was cooled, diluted with about an equal volume of 1 N aqueous potassium hydroxide and washed about 4 times with ether. The cold, aqueous layer was neutralized with 12 N hydrochloric acid and the neutralized solution was extracted 4 times with 100–200 ml portions of ethyl acetate. The combined organic layers were back-extracted with saturated brine solution and saturated aqueous sodium bicarbonate. The organic layer was dried over an agent such as magnesium sulfate followed by filtration, removal of the solvent in vacuo and recrystallization of the residue from an appropriate organic solvent. The Examples prepared and their characterizing data are listed in Table 1.

Table 1

Examples of spiro-polycyclicimidazolinedione derivatives and their physical characterizing data

| Example | Compound | mp | Analysis | | |
|---|---|---|---|---|---|
| | | | C | N | H |
| 1 | 2',3'-dihydro-spiro[imidazolidine-4,4'-[4'H]-naphtho[2,1-b]thiopyran]-2,5-dione | 240–1° | cal'd 63.03<br>f'd 63.36 | 4.43<br>4.52 | 9.48<br>9.20 |
| 2 | 2',3'-dihydro-7'-methoxy-spiro[imidazolidine-4,4'-[4'H]-naphtho[1,,2-b]pyran]-2,5-dione | 275°(d) | cal'd 64.42<br>f'd 64.16 | 4.73<br>4.94 | 9.39<br>9.20 |
| 3 | 1',2',3',4'-tetrahydro-spiro[imidazolidine-4,1'-benz[a]anthracene]-2,5-dione | 298°(d) | cal'd 75.93<br>f'd 75.57 | 5.10<br>5.31 | 8.96<br>8.75 |
| 4 | 2',3'-dihydro-spiro[imidazolidine-4,4'-[4'H]-naphtho[1,2-b]thiopyran]-2,5-dione | 153–154° | cal'd 62.72<br>f'd 62.84 | 4.62<br>4.72 | 9.14<br>9.16 |
| 5 | 5',6'-dihydro-6'-chloro-spiro[imidazolidine-4,4'-[4'H]-naphtho[1,2-b]pyran]-2,5-dione | 215–216° | cal'd 59.51<br>f'd 59.70 | 3.66<br>3.97 | 9.26<br>9.02 |
| 6 | 2',3'-dihydro-spiro[imidazolidine-4,4'-[4'H]-naphtho[2,1-b]pyran]-2,5-dione | 295°(d) | cal'd 67.15<br>f'd 66.85 | 4.51<br>4.75 | 10.44<br>10.10 |
| 7 | 1',2',3',4'-tetrahydro-spiro[imidazolidine-4,1'-phenanthrene]-2,5-dione | 300° | | | |

Table 1-continued

Examples of spiro-polycyclicimidazolinedione derivatives and their physical characterizing data

| Example | Compound | mp | | Analysis | | |
|---|---|---|---|---|---|---|
| | | | | C | N | H |
| 8 | 2',3'-dihydro-spiro[imidazoli-dine-4,1'-phenalene]-2,5-dione | 233–235° | cal'd | 71.41 | 4.79 | 11.10 |
| | | | f'd | 71.47 | 4.84 | 11.09 |
| 9 | 2',3'-dihydro-spiro[imidazolidine-4,4'-[4'H]-naphtho[1,2-b]pyran]-2,5-dione | 253–254° | cal'd | 64.97 | 4.72 | 10.10 |
| | | | f'd | 65/13 | 4.51 | 9.99 |
| 10 | 1',2',3',4'-tetrahydro-spiro[imidazolidine-4,4'-phenanthrene]-2,5-dione | 238–240° | cal'd | 72.16 | 5.29 | 10.52 |
| | | | f'd | 71.86 | 5.47 | 10.42 |

ALDOSE REDUCTASE INHIBITORY ACTIVITY

The Examples of spiro-polycyclicimidazolidinedione derivatives prepared above were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The drug was tested at a concentration of $10^{-4}$ M and optionally at lower concentrations and the results are expressed as percent inhibition of enzyme activity.

| Polycyclicimidazolidinedione Derivative Example | % Inhibition $10^{-4}$ M |
|---|---|
| 1 | 59 |
| 2 | 94* |
| 3 | 26 |
| 4 | 100 |
| 5 | 78* |
| 6 | 78* |
| 7 | 86* |
| 8 | 71 |
| 9 | 72 |
| 10 | 60 |

*This number represents an average of 2 or 3 tests.

INHIBITION OF SORBITOL ACCUMULATION

Some of the Examples of spiro-polycyclicimidazolidinedione derivatives prepared above were also tested for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose level indicated at 4, 8 and 24 hours following the administration of streptozotocin. The results obtained in this manner are presented in terms of percent inhibition (%) afforded by the test compound as compared to the case where no compound was administered (i.e., the untreated animal where sorbitol levels normally rise from approximately 50–100 mM/g tissue to as high as 400 mM/g tissue in the 27-hour test period).

| Polycyclicimidazolidinedione Derivative Example | % Inhibition at Dose of 1.5 mg/kg |
|---|---|
| 2 | no effect |
| 4 | 32 |
| 5 | * |
| 6 | no effect |
| 7 | no effect |
| 8 | * |
| 9 | 30 |

*Example 5 was tested at 5.0 mg/kg and showed 58% inhibition. Example 8 was tested at 5.0 mg/kg and showed 28% inhibition.

What is claimed is:

1. A spiro-polycyclicimidazolidinedione derivative of the formula

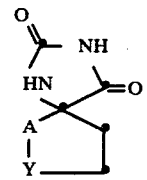

or its pharmaceutically acceptable metallic salt, wherein:

A is naphth-$\alpha,\beta$-o of the formula

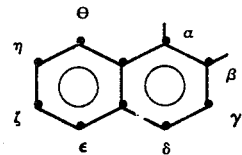

anthracen-$\alpha,\beta$-o of the formula

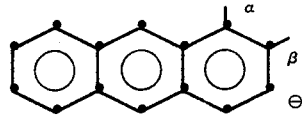

or substituted naphth-$\alpha,\beta$-o having 1 or 2 identical substituents selected from methyl, chloro or bromo; and Y is $CH_2$, S, SO, $SO_2$ or O;

or A and Y taken together are a naphth-$\alpha,\Theta$-o ring of the formula

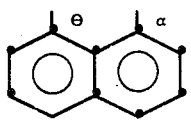

2. A spiro-polycyclicimidazolidinedione derivative of claim 1 wherein A is naphth-$\alpha,\beta$-o and Y is $CH_2$, S or O.

3. The spiro-polycyclicimidazolidinedione derivative of claim 1 wherein A is naphth-$\alpha,\beta$-o, Y is S and S joins the naphth-$\alpha,\beta$-o ring at the $\beta$ position.

4. The spiro-polycyclicimidazolidinedione derivative of claim 1 wherein A is naphth-$\alpha,\beta$-o, Y is S and S joins the naphth-$\alpha,\beta$-o at the $\alpha$ position.

5. The spiro-polycyclicimidazolidinedione derivative of claim 1 wherein A is naphth-$\alpha,\beta$-o, Y is O and O joins the naphth-$\alpha,\beta$-o ring at the $\alpha$ position.

6. The spiro-polycyclicimidazolidinedione derivative of claim 1 wherein A is $\epsilon$-methoxynaphth-$\alpha,\beta$-o, Y is O and O joins the $\epsilon$-methoxynaphth-$\alpha,\beta$-o at the $\alpha$ position.

7. The spiro-polycyclicimidazolidinedione derivative of claim 1 wherein A is $\delta$-chloronaphth-$\alpha,\beta$-o, Y is O and O joins the $\delta$-chloronaphth-$\alpha,\beta$-o at the $\alpha$ position.

8. The spiro-polycyclicimidazolidinedione derivative of claim 1 wherein A is naphth-$\alpha,\beta$-o, Y is $CH_2$ and $CH_2$ joins the naphth-$\alpha,\beta$-o at the $\alpha$ position.

9. The spiro-polycyclicimidazolidinedione derivative of claim 1 wherein A and Y taken together are naphth-$\alpha,\theta$-o.

10. A pharmaceutical formulation of a spiro-polycyclicimidazolidinedione derivative of claim 1, which comprises: a combination of a pharmaceutically-acceptable carrier material and the derivative in an amount effective to inhibit harmful, in vivo enzymatic reduction of aldoses or to prevent or alleviate diabetes-associated complications.

11. A method of treating a diabetic host to inhibit harmful, in vivo enzymatic reduction of aldoses or to prevent or alleviate diabetes-associated complications, which comprises: administering to the host an effective amount of a derivative of claim 1.

* * * * *